(12) United States Patent
Yano et al.

(10) Patent No.: US 9,835,569 B2
(45) Date of Patent: Dec. 5, 2017

(54) MAGNETIC MEASUREMENT SYSTEM AND APPARATUS UTILIZING X-RAY TO MEASURE COMPARATIVELY THICK MAGNETIC MATERIALS

(71) Applicants: TOYOTA JIDOSHA KABUSHIKI KAISHA, Toyota-shi, Aichi (JP); INTER-UNIVERSITY RESEARCH INSTITUTE CORPORATION HIGH ENERGY ACCELERATOR RESEARCH ORGANIZATION, Tsubaki-shi, Ibaraki (JP)

(72) Inventors: Masao Yano, Sunto-gun (JP); Kanta Ono, Tsukuba (JP)

(73) Assignees: TOYOTA JIDOSHA KABUSHIKI KAISHA, Toyotoa-Shi (JP); INTER-UNIVERSITY RESEARCH INSTITUTE CORPORATION HIGH ENERGY ACCELERATOR RESEARCH ORGANIZATION, Tsukuba-Shi (JP)

( * ) Notice: Subject to any disclaimer, the term of this patent is extended or adjusted under 35 U.S.C. 154(b) by 0 days.

(21) Appl. No.: 15/471,412

(22) Filed: Mar. 28, 2017

(65) Prior Publication Data

US 2017/0199135 A1   Jul. 13, 2017

Related U.S. Application Data

(63) Continuation-in-part of application No. 14/496,966, filed on Sep. 25, 2014.

(30) Foreign Application Priority Data

Sep. 25, 2013 (JP) .................................. 2013-198163

(51) Int. Cl.
  *G01R 33/12* (2006.01)
  *G01N 23/083* (2006.01)

(52) U.S. Cl.
  CPC ........... *G01N 23/083* (2013.01); *G01R 33/12* (2013.01); *G01N 2223/315* (2013.01)

(58) Field of Classification Search
  CPC ................. G01N 23/063; G01N 27/72; G01N 2223/405; G01N 23/04; G01N 2223/315; G01N 23/083; G01R 33/12
  (Continued)

(56) References Cited

U.S. PATENT DOCUMENTS 3,967,902 A   7/1976  Steinberg
4,003,663 A   1/1977  Steinberg
(Continued)

FOREIGN PATENT DOCUMENTS

JP    5-45304 A     2/1993
JP    2010-151455 A  7/2010
(Continued)

OTHER PUBLICATIONS

Ono et al., "Element-Specific Magnetic Domain Imaging of (Nd, Dy)-Fe—B Sintered Magnets Using Scanning Transmission X-Ray Microscopy," IEEE Transactions on Magnetics, Oct. 2011, vol. 47, No. 10, pp. 2672-2675.
(Continued)

*Primary Examiner* — Jay Patidar
(74) *Attorney, Agent, or Firm* — Westerman, Hattori, Daniels & Adrian, LLP

(57) ABSTRACT

A magnetic measurement system includes an X-ray source, a monochromator that converts right- and left-polarization X-ray into right- and left-monochromatic X-ray, an aperture slit that allows the right- and left-monochromatic X-ray to pass through, an analytical section, and piezoelectric scanning devices. The analytical section has a Fresnel zone plate that receives and focuses the right- and left-monochromatic X-ray on a single point being 10 nm or less wide of a magnetic sample, an order-sorting aperture that allows the focused X-ray to selectively pass through, a sample-stage that sets a comparatively thick magnetic sample that is more
(Continued)

than 150 nm thick and less than or equal to 1000 nm thick to be irradiated with the X-ray, and an X-ray-detector that detects transmittance of transmission X-ray passing through the comparatively thick sample and that generates X-ray magnetic circular dichroism (XMCD) data by directly measuring the detected transmittance of the transmission X-ray.

2 Claims, 9 Drawing Sheets

(58) Field of Classification Search
USPC .............................................. 324/228, 244.1
See application file for complete search history.

(56) References Cited

U.S. PATENT DOCUMENTS

| | | | |
|---|---|---|---|
| 6,389,101 B1 | 5/2002 | Levine et al. | |
| 6,917,472 B1 | 7/2005 | Yun et al. | |
| 2004/0246479 A1 | 12/2004 | Cartlidge et al. | |
| 2009/0135486 A1 | 5/2009 | McNulty | |
| 2015/0174272 A1 | 6/2015 | Velez Tirado et al. | |

FOREIGN PATENT DOCUMENTS

| | | |
|---|---|---|
| JP | 2011-66005 A | 3/2011 |
| JP | 2012-145533 A | 8/2012 |

OTHER PUBLICATIONS

Alvarenga et al., "X-ray Magnetic Circular Dichroism in Fe/Nio Thin Films," Journal of Magnetism and Magnetic Materials, 2001, vol. 233. pp. 74-77.
Schütz et al., "Absorption of Circularly Polarized X Rays in Iron," Physical Review Letters, 1987, vol. 58, No. 7, Feb. 16, 1987, pp. 737-740.
"3D Nano-ESCA Station," University of Tokyo.
"Transmission Electron Microscope of Surface of Roll Fabricated by Focused Ion Beam," JFE Techno-Research Corporation.

MAGNETIC MEASUREMENT SYSTEM AND APPARATUS UTILIZING X-RAY TO MEASURE COMPARATIVELY THICK MAGNETIC MATERIALS

CROSS-REFERENCE TO RELATED APPLICATIONS

This application is a Continuation in-Part application Ser. No. 14/496,966 filed Sep. 25, 2014, which claims the benefit of priority Japanese Patent Application No. JP2013-198163, filed on Sep. 25, 2013, the entire contents of which are incorporated herein by reference.

TECHNICAL FIELD

The present invention relates to the magnetic measurement system and apparatus.

BACKGROUND

The paper 1 has reported the original X-ray magnetic circular dichroism as follows: a magnetic sample is placed in the external strong magnetic field, an internal magnetization direction of the magnetic sample is aligned with one direction, then the sample is irradiated with circular polarization X-ray while the external magnetic field direction is alternately inverted, resultantly, intensity of transmission X-ray passing the sample is changed in accordance with whether the external magnetic field direction is parallel or anti-parallel to the polarization light direction, the intensity change appears remarkably at a neighborhood of X-ray absorption edge for the constituent element of the magnetic sample. The paper 2 has reported element-specific magnetic domain imaging of (Nd, Dy)—Fe—B sintered magnets using scanning transmission X-ray microscopy. Here, the paper 2 disclosed in experimental to focus circularly polarized monochromatic synchrotron radiation X-rays on a single point being about 30 nm wide of the magnetic sample being from more than 50 nm to 150 nm thick using a Fresnel zone plate (FZP) and to detect the X-ray magnetic circular dichroism (XMCD) of the magnetic sample using a detector controlled by an interferometer-controlled piezo stage. However, the method disclosed by the paper 2 could not measure a comparable thick magnetic sample that is more than 150 nm thick, because the circularly polarized monochromatic X-ray having a focused size of about 30 nm is too weak to penetrate the magnetic sample being more than 150 nm thick. Applying the above X-ray magnetic circular dichroism, very old method such as the patent literature 1 has been presented to observe magnetic samples. The patent literature 1 presented the method and apparatus to observe magnetic domain by XMCD as follows: the intensity ($I_0$) of incident X-ray and intensity ($I_t$) of transmission X-ray passing the sample are measured, $\mu_{RXt}=\ln(I_0/I_t)$ and $\mu_{LXt}=\ln(I_0/I_t)$ are calculated using the observed intensity ($I_o$) and observed intensity ($I_t$), $M=(\mu_{RXt}-\mu_{LXt})/(\mu_{RXt}+\mu_{LXt})=(\mu_R-\mu_L)/(\mu_R+\mu_L)$ is calculated using [$\mu_{RXt}$] and [$\mu_{LXt}$] and M is transformed into electronic signal for imaging, here, $\mu_R$ and $\mu_L$ are X-ray absorption coefficient for right-circular polarization X-ray and left-circular polarization X-ray, respectively, and t is thickness of the sample. However, the method was impracticable because focusing of X-ray is no good, sensitivity of X-ray detection is very low, and X-ray transmittance for right-circular polarization X-ray and left-circular polarization X-ray are calculated from observed X-ray intensity $\ln(I_0/I_t)$ but indirectly observed.

Observation, structural analysis and elemental analysis of the structures and chemical and physical states of magnetic sample surfaces or their neighborhood have been studied using the secondary electrons which are emitted from the sample surfaces by irradiating the observed areas of the sample with electron beams or exciting light. For example, the patent literature 2 presented the method to form observation images of microscopic structures of the sample. However, the above conventional method has included several difficult problems: (1) the conventional method is merely able to observe magnetic characteristics in the region from uppermost surfaces of the sample to several nanometers in depth but unable to observe them over several nanometers in depth because any electrons to generate from places deeper than several nanometers cannot get out of the sample surfaces. Because, the method is the one to detect the secondary electrons that are emitted from the magnetic sample on absorption of synchrotron radiation light, (2) the conventional method has essentially undesirable problem that the observed analytical result does not always show true magnetic properties of the bulk due to interruption effect of oxidized layers in the uppermost surfaces, (3) the conventional method is undesirable to observe the magnetic sample within magnetic field because of an applied magnetic field to exert influence on the detection of the secondary electrons. From these reasons, it has been very difficult to measure in practice the magnetized structure in the inside of microparticles.

RELATED ART

[Paper 1] Physical Review Letters, vol. 58, pp. 737-740 (1987)
[Paper 2] Kanta ONO, et al., IEEE TRANSACTIONS ON MAGNETICS, VOL. 47, NO. 10, OCTOBER 2011, pp. 2672-2675
[Patent Literature 1] JP-A-1993-045304
[Patent Literature 2] JP-A-2010-151455

DISCLOSURE OF THE INVENTION

The magnetic characteristic of magnetic body is almost determined by the magnetic properties in the micro-region. Therefore, it is necessary for the development of new magnetic materials to assign magnetic properties of the micro-particles. The conventional methods such as the above patent literature 1, Kerr effect microscope, magnetic force microscope, photo-electron microscope and the like, which have been known to obtain the magnetic information such as magnetic domain and magnetic moment, make it possible to observe the magnetic properties in the uppermost sample surfaces or averaged magnetic properties of polycrystalline materials. However, the conventional methods have been unable to observe even the magnetic properties of a single micro-particle as explained above.

The object of the present invention, in view of the above described circumstances, to provide the system and apparatus that are capable of measuring true magnetic characteristic of crystal grains composing magnetic polycrystalline materials.

Measure for Solving the Problem

To achieve the above object, the present invention provides the system and apparatus that are capable of measuring the magnetic characteristic of sample within external magnetic field by X-ray magnetic circular dichroism. In particular, the present invention provides the system and apparatus to measure accurately and directly magnetic characteristic of very thick samples of 1 μm. In particular, the present invention is very effective for measuring the magnetic sample that is more than 150 nm thick and less than or equal to 1000 nm thick. However, the magnetic sample being more than 1000 nm in thick is usually unnecessary for the measurement of the magnetic sample because almost crystalline-grains contained in the polycrystalline magnetic sample are smaller than 1000 nm in size. The measurement of the above thick magnetic sample is for the first time achieved by focusing a single point being 10 nm or less wide of circularly polarized monochromatic X-ray on the magnetic sample, using the FZP. The focused X-ray-size being 10 nm or less wide makes the focused X-ray nine times as strong as that of the paper 2 and makes the focused X-ray penetrate the magnetic sample nine times as thick as that of the paper 2. The focused size being 10 nm or less wide can be achieved by piezoelectric devices that control X-, Y- and Z-stages of the analytical section, which includes the sample-stage, with an accuracy in nanometers.

In one aspect of the present invention, a magnetic measurement system or apparatus includes an X-ray source, a monochromator, an aperture slit, an analytical section, and piezoelectric scanning devices. The monochromator converts right- and left-polarization X-ray of the X-ray source into right- and left-monochromatic X-ray. The aperture slit allows the right- and left-monochromatic X-ray converted by the monochromator to pass through. The analytical section has a combination of a Fresnel zone plate (FZP) that receives and focuses the right- and left-monochromatic X-ray on a single point being 10 nm or less wide of a magnetic sample, an order-sorting aperture (OSA) that allows the X-ray focused by the FZP to selectively pass through, a sample-stage that sets a comparatively thick magnetic sample that is more than 150 nm thick and less than or equal to 1000 nm thick to be irradiated with the X-ray, and an X-ray-detector that detects transmittance of transmission X-ray passing through the comparatively thick sample set by the sample-stage and that generates X-ray magnetic circular dichroism (XMCD) data by directly measuring the detected transmittance of the transmission X-ray. The piezoelectric scanning devices accurately control X-, Y- and Z-stages of the analytical section with an accuracy in nanometers which includes the sample-stage of the analytical section. This system and apparatus can accurately generate XMCD data by directly measuring transmittance of transmission X-ray passing through the comparatively thick magnetic sample even within an external magnet field.

Advantages of the Invention

The present invention is able to directly measure transmittance of transmission X-ray passing the sample placed within external magnetic field, using the Avalanche photodiode to measure photo-count of X-ray magnetic circular dichroism. Therefore, the present invention makes it possible to carry out high sensitive and high precise measurement of magnetic sensitivity, magnetic state and magnetic structure of the bulk sample. Accordingly, the present invention makes it possible to measure the magnetic characteristic of single crystal grains in the sample that is more than 150 nm thick and less than or equal to 1000 nm thick.

EMBODIMENTS FOR CARRYING OUT THE INVENTION

First the sample to be measured is cut into a microtome section of 50 nm~1000 nm in thickness. Preferable thickness of microtome section can be determined mainly by sample material, kinetic energy of used x-ray and transmittance of X-ray. For the present invention, a use of X-ray transmittance of 1% or more is sufficient for the measurement of micro-crystal grains. The thickness of microtome section is preferably 1000 nm or less, more preferably 150 nm~1000 nm. The preparation of the microtome section of 150 nm~1000 nm in thickness makes it possible to measure magnetic characteristic of micro-crystal grains and imaging with resolution of 10 nm or less, accordingly makes it possible to study local magnetic sensitivity induced by an applied magnetic field.

Figure 1:
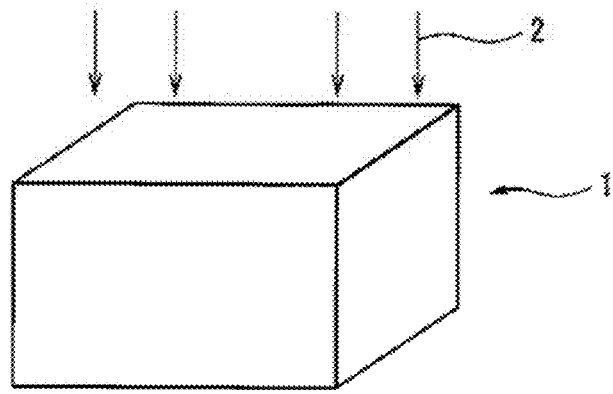
FIG. 1 is a cross-eye view showing the sample before etching.
Figure 2:
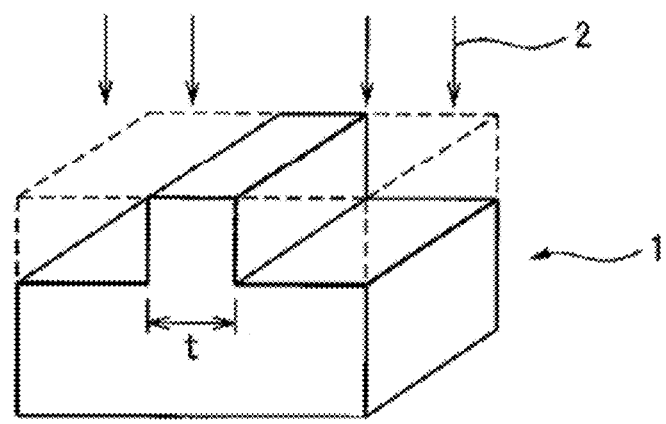
FIG. 2 is a cross-eye view showing the sample after etching.
Figure 3:
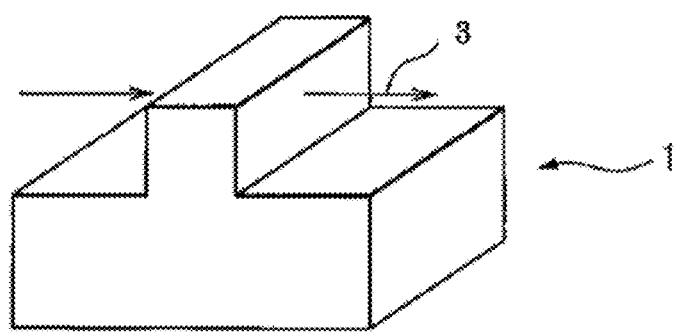
FIG. 3 is a cross-eye view showing the observation process.

For the preparation of microtome section, various methods can be used. For the preparation of microtome section of 1000 nm or less, the etching using focused ion beams is preferable. For example, the sample 1 as shown in FIG. 1 is etched using the focused ion beam 2 followed by obtaining a microtome section 1000 nm or less thick as shown in FIG. 2.

As the sample, various materials, for example, soft magnetic materials, hard magnetic materials, magnetic materials with plural magnetic phases, can be applied. As an apparatus to generate the focused ion beam 2, a usual focused ion beam machine comprising an ion beam gun and optic system to generate Ga-ion beam and scanning system to scan ion beams on the sample surfaces can be utilized.

After etching the sample using the focused ion beam 2, an observation place is irradiated with the X-ray 3, followed by detection the transmission X-ray to measure magnetic characteristic of the sample.

X-ray to be applied the sample is preferably circular polarization X-ray focused into 10 nm in beam size. In practice, the X-ray 3 generated by an X-ray generator which is capable of generating right-circular polarization X-ray and left-circular polarization X-ray enters a measurement place of the sample 1, successively the transmission X-ray is detected by a detector. The intensity IR of the transmission X-ray corresponding to right-circular polarization X-ray and the intensity IL of the transmission X-ray corresponding to left-circular polarization X-ray are alternately measured, successively the difference between them, that is, XMCD, can be detected. This measurement is corresponding to the magnetization in the inside of the X-ray incident position. Successively, the same measurement is carried out while two-dimensional (2-D)-scanning the sample, thus a 2-D-data is obtained. As another method, the X-ray absorption parallel to the magnetic field direction of the sample and that in the anti-parallel direction are measured using either right-circular polarization X-ray or left-polarization X-ray, the difference between them, that is, XMCD, can be also measured.

Figure 4:
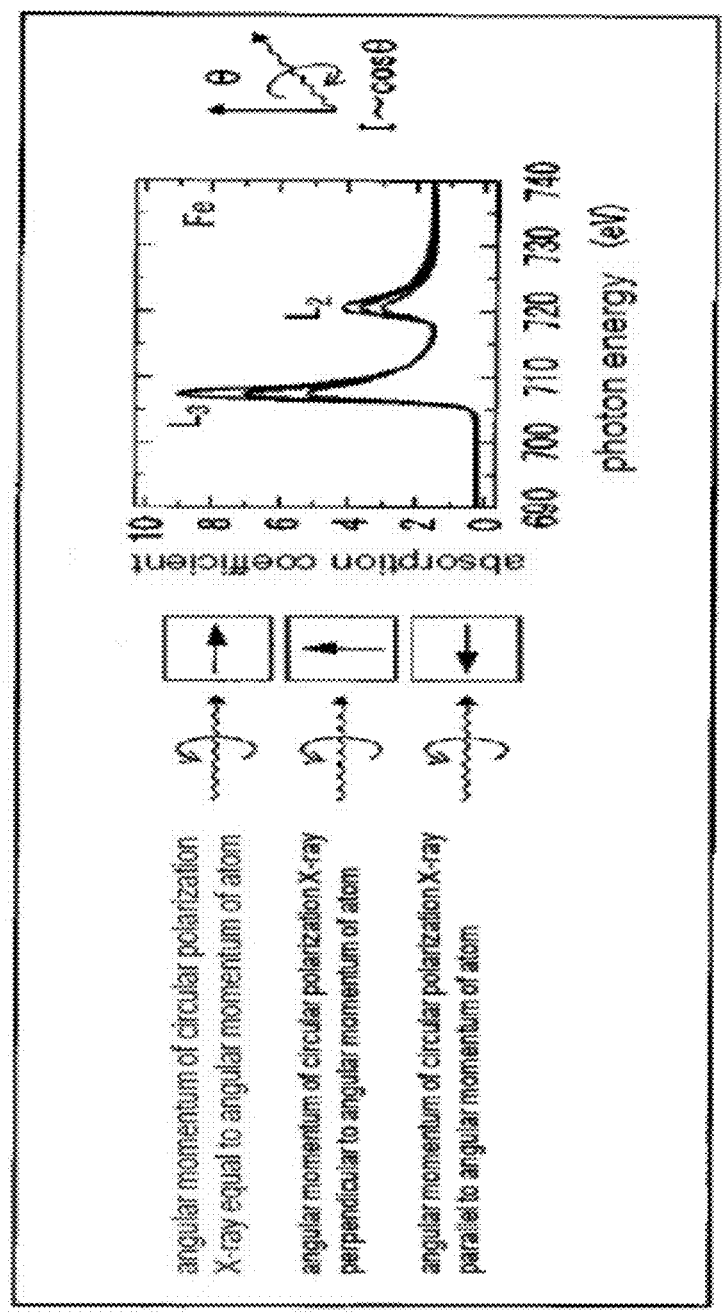
FIG. 4 is a schematic view illustrating the principle of X-ray magnetic circular dichroism (XMCD).

Further explaining in detail, magnetic information can be obtained using the principle of XMCD as shown in FIG. 4. The method has the element-selectivity, that is, the method is capable of measuring the direction of magnetic moment for a specific element by adjusting X-ray energy with an excitation energy gap between specific electron orbital.

As shown in FIG. 4, an absorption spectrum changes in accordance with the direction of angular momentum of circular polarization light and the direction of angular momentum of atom. The basic magnetic properties such as orbital angular momentum, spin angular momentum and magnetic momentum can be measured from (1) the measurement of angular momentum of circular polarization X-ray and that of atom in the case both momentums are parallel; (2) the measurement of angular momentums of circular polarization X-ray and that of atom in the case both momentums are anti-parallel; (3) the difference between them, that is, XMCD.

Figure 5:
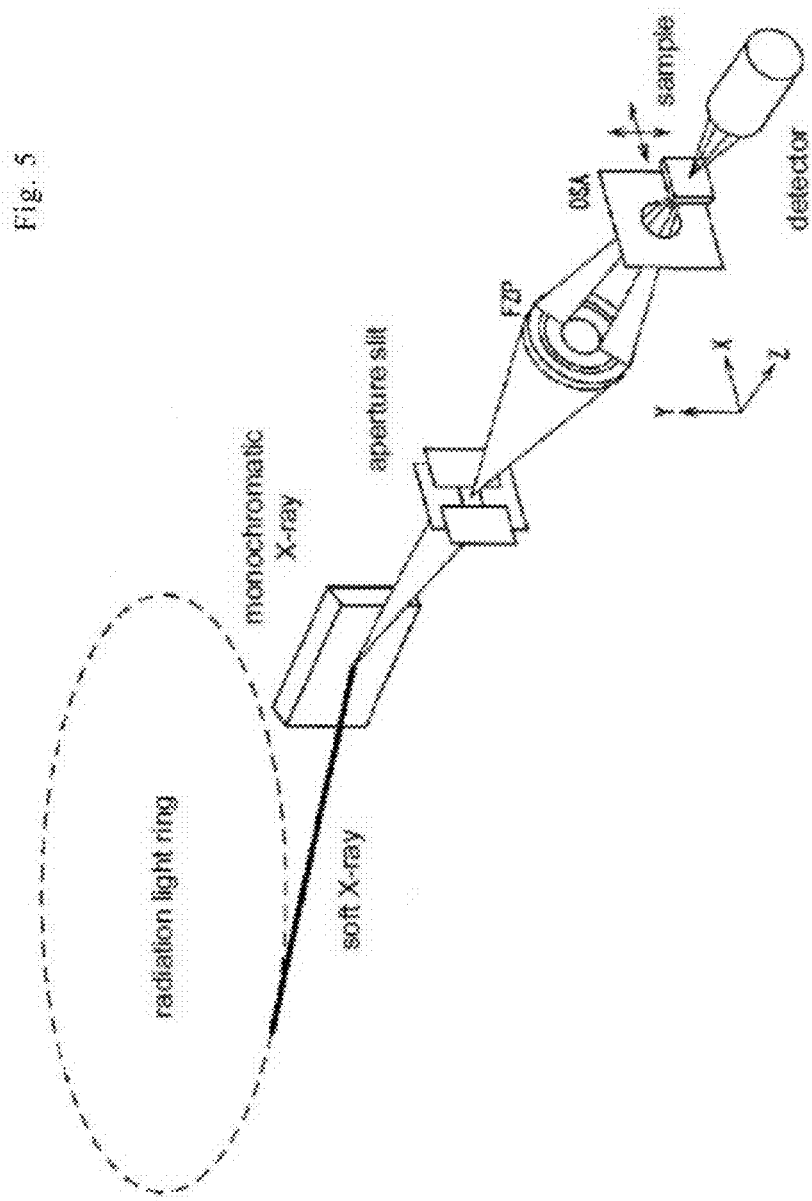
FIG. 5 is a configuration of the present apparatus equipping a scanning transmission electron microscope to carry out the present method.

As shown in FIG. 5, the present measurement system comprises a radiation source, a monochromator to disperse white radiation into monochromatic X-ray, an aperture slit to enter X-ray of the radiation source into an analytical section, the analytical section equipping a combination of Fresnel zone plate and order-sorting aperture to focus X-ray flux passing the aperture slit, a sample-stage to set a sample to be irradiated with X-ray and an X-ray-detector to detect transmission X-ray passing the sample; which is characterized by the measurement of X-ray magnetic circular dichroism of X-ray passing the sample within magnetic field or nonmagnetic field. The XMCD at each sample place can be measured through precisely scanning the sample stage and using focused radiation light.

Figure 6:
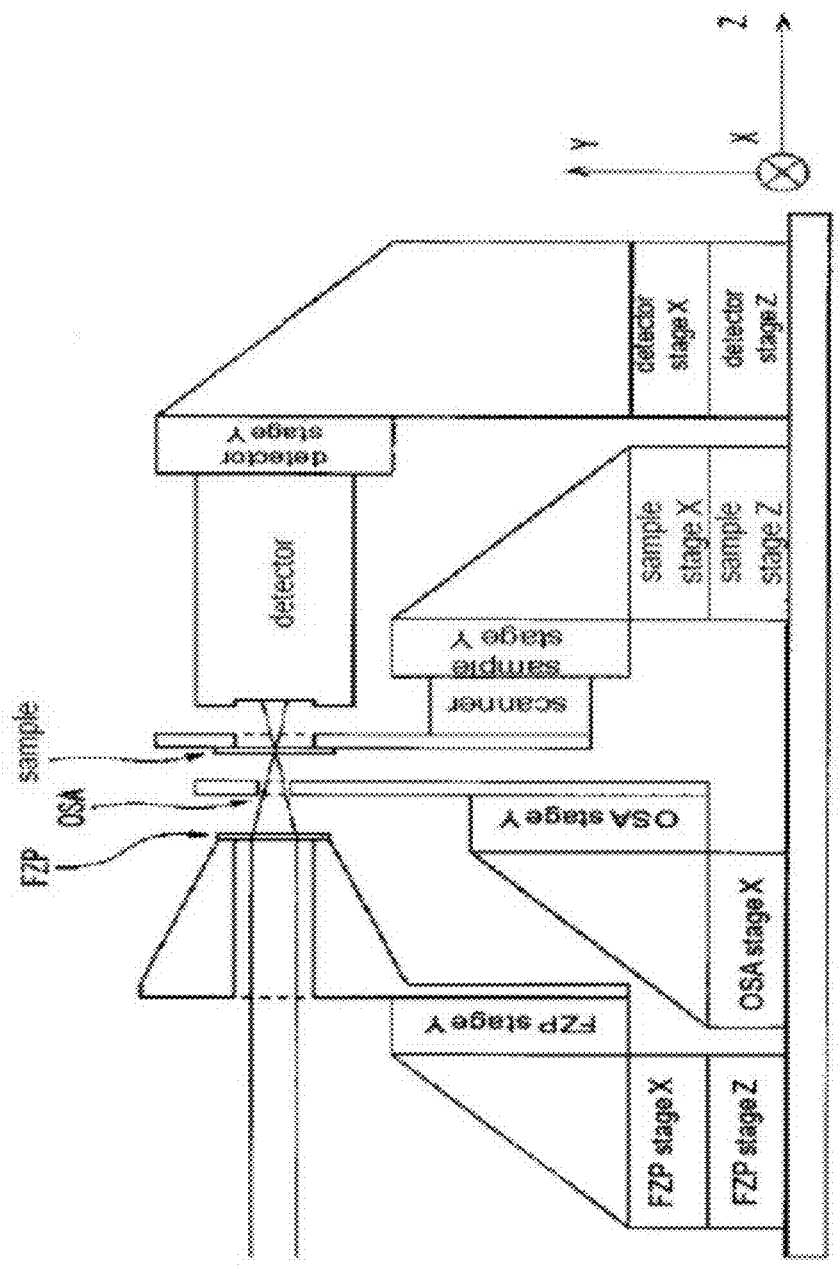
FIG. 6 is a configuration of the present apparatus to carry out the present method.

As shown in FIG. 6, the present measurement apparatus comprises the analytical section equipping a combination of Fresnel zone plate (FZP) and order-sorting aperture (OSA) to focus X-ray flux passing the aperture slit, the sample stage to set a sample to be irradiated with X-ray and the X-ray-detector equipping the Avalanche photodiode to detect transmittance of transmission X-ray passing the sample. The FZP, OSA, sample-stage and X-ray-detector are equipping piezoelectric devices, therefore their X-, Y- and Z-stages can be controlled to an accuracy of nanometers. For the efficient X-ray detection under a vacuum and magnetic field, the Avalanche photodiode (APD) having dynamic ranges and optical fibers which is used within external magnetic field is preferable. Also, the exclusion of large-generating parts such as motors and laser prevents the resolution of APD from thermal drift. Therefore, such exclusion is necessary to measure XMCD of a single particle in the nano-crystalline magnet. In addition, for the measurement in the magnetic field, a combination system of superconductive magnet and use of non-magnetic parts and devices is preferable.

A bulk sample of $Nd_2Fe_{14}B$ or $Sm_2Fe_{17}N_3$ is used as the sample. The sample is fabricated using focused ion beams, followed by measuring X-ray transmittance at each sample position. The measurement of X-ray transmittance for the $Nd_2Fe_{14}B$ sample or $Sm_2Fe_{17}N_3$ sample is based on the Nd-absorption-edge X-ray energy (980.4 eV) or Sm-absorption-edge X-ray energy (1083.3 eV), respectively. The result is shown in FIG. 7.

Figure 7:
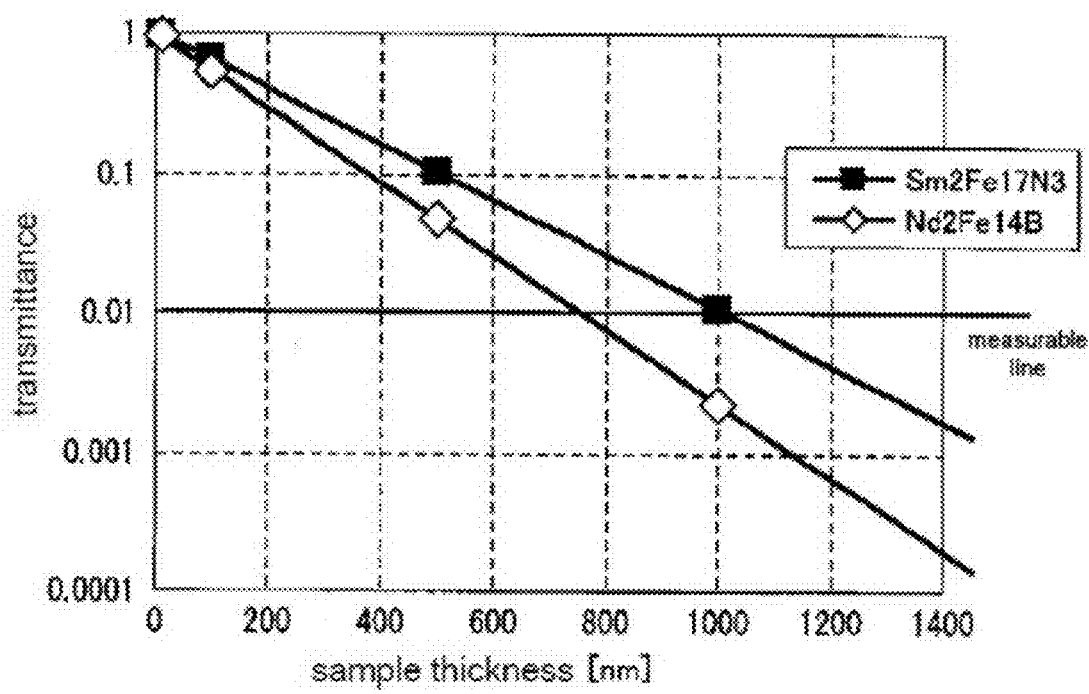
FIG. 7 shows a relationship between X-ray transmittance and thickness of the sample.

From the result of FIG. 7, it is found that the $Nd_2Fe_{14}B$ sample is measurable in the range 750 nm or less, 500 nm or less, 100 nm or less in thickness and that the $Sm_2Fe_{17}N_3$ sample is measurable in the range 1000 nm or less, 500 nm or less, 100 nm or less in thickness.

Figure 8:
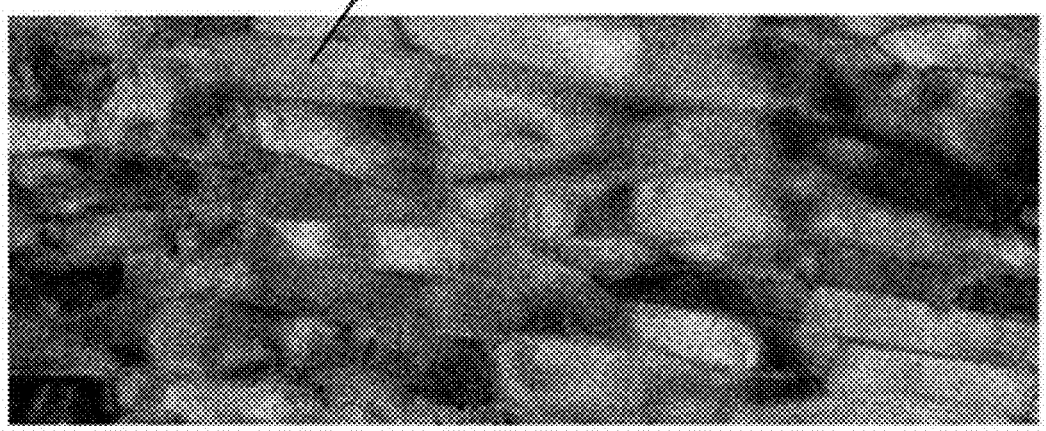
FIG. 8 is a transmission electron microscope (TEM) image of the sample plane.

A bulk sample of Nd—Fe—B magnet is used for the sample is observed. From FIG. 8, the observed crystalline particle is estimated to be about 50 nm-100 nm in size.

Figure 9:
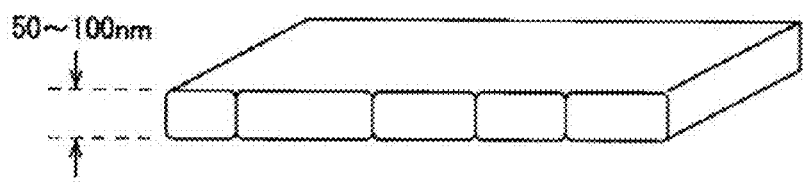
FIG. 9 is a cross-eye view showing a sample geometry after processing.
Figure 10:
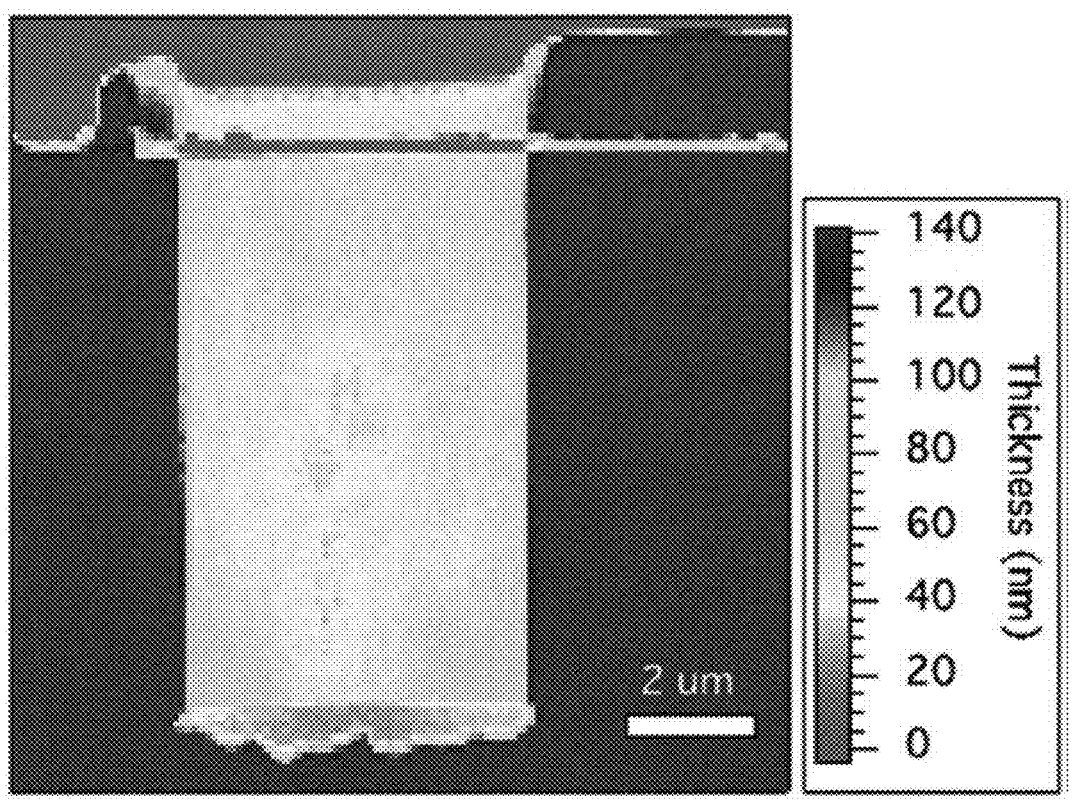
FIG. 10 shows thickness-distribution obtained from intensity of the transmission X-ray.

Next, the fabricated sample as shown in FIG. 9 is etched using focused ion beam. X-ray transmittance of the obtained sample is measured, followed by determining thickness distribution as shown in FIG. 10. The thickness of the sample can be determined from the following equation.

$$t = \lambda \ln(I_0/I)$$

where, t is a sample thickness, λ is substance-specific X-ray transmittance, $I_0$ is intensity of X-ray irradiation, I is intensity of transmission X-ray.

As shown in FIG. 10, the sample is found to be fabricated into 50 nm~1000 nm in thickness.

Figure 11:
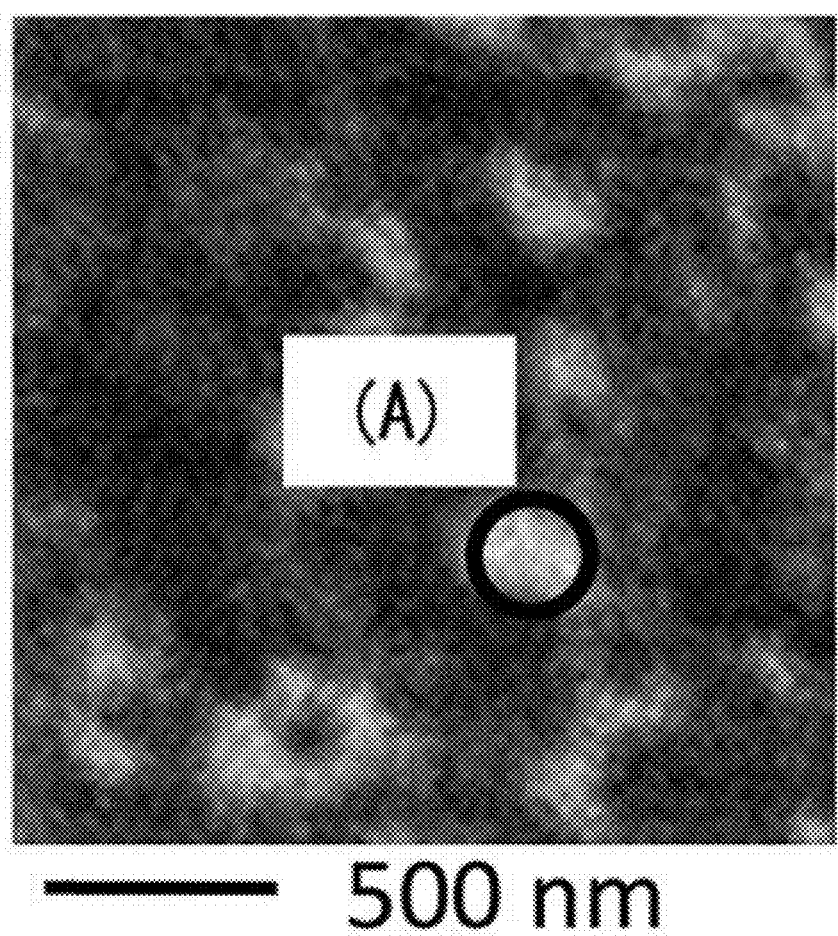
FIG. 11 shows an observed XMCD interval distribution.
Figure 12:
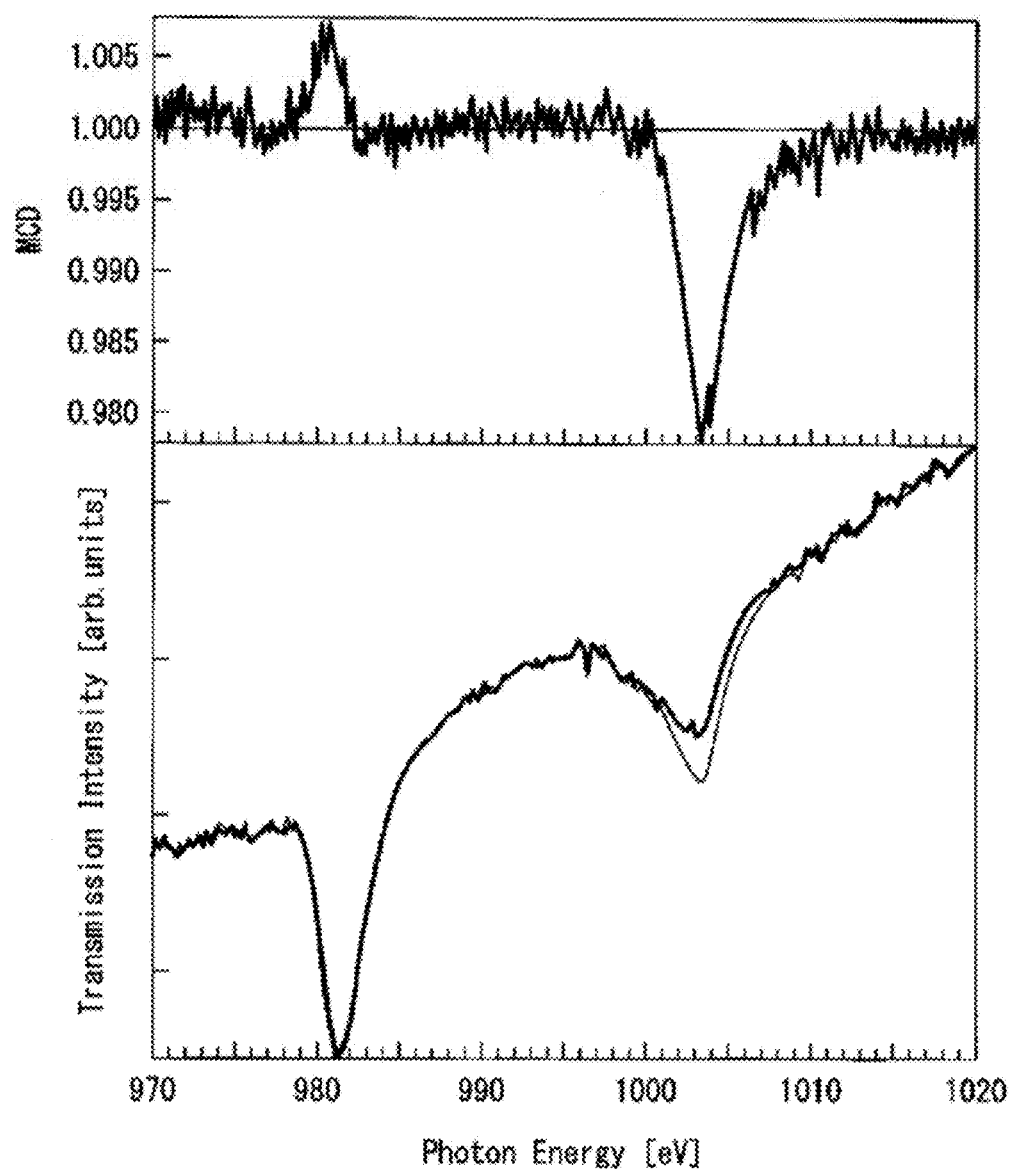
FIG. 12 shows a result of magnetic characteristic measurement.

Next, the fabricated sample is irradiated with circular polarization X-ray, followed by measuring magnetic characteristic. FIG. 11 shows a XMCD space distribution. In FIG. 11, the difference in contrasting density of white and black colors shows the difference for the direction of magnetic moment corresponding to the magnetic domain phase of magnetic body. The magnetic characteristic at the part (A) in FIG. 11 is found to have two peaks at 981 eV and 1003 eV, respectively, as shown in FIG. 12. From the spectrum analysis, it is found that the magnetism property such as spin magnetic momentum and orbital magnetic momentum can be measured for a single crystal particle.

EXPLANATION OF REFERENCE CHARACTERS 1 sample
2 focused ion beam
3 X-ray

The invention claimed is:
1. A magnetic measurement system, comprising:
an X-ray source;
a monochromator that converts right- and left-polarization X-ray of the X-ray source into right- and left-monochromatic X-ray;
an aperture slit that allows the right- and left-monochromatic X-ray converted by the monochromator to pass through;
an analytical section having a combination of a Fresnel zone plate (FZP) that receives and focuses the right- and left-monochromatic X-ray on a single point being 10 nm or less wide of a magnetic sample, an order-sorting aperture (OSA) that allows the X-ray focused by the FZP to selectively pass through, a sample-stage that sets the comparatively thick magnetic sample that is more than 150 nm thick and less than or equal to 1000 nm thick to be irradiated with the X-ray, and an X-ray-detector that detects transmittance of transmission X-ray passing through the comparatively thick sample set by the sample-stage and that generates

X-ray magnetic circular dichroism (XMCD) data by directly measuring the detected transmittance of the transmission X-ray;

piezoelectric scanning devices that accurately control X-, Y- and Z-stages of the analytical section with an accuracy in nanometers which includes the sample-stage of the analytical section; wherein, the system accurately generates XMCD data by directly measuring transmittance of transmission X-ray passing through the comparatively thick magnetic sample even within an external magnet field.

2. A magnetic measurement apparatus, comprising:

an analytical section having a combination of a Fresnel zone plate (FZP) that focuses right- and left-polarization X-ray on a single point being 10 nm or less wide of a polycrystalline magnetic sample, an order-sorting aperture (OSA) that allows the X-ray focused by the FZP to selectively path through, a sample-stage that is configured to set the polycrystalline magnetic sample that is more than 150 nm thick and less than or equal to 1000 nm thick to be irradiated with the X-ray passing the OSA, an X-ray-detector that, using an Avalanche photodiode, detects transmittance of transmission X-ray passing through the polycrystalline magnetic sample, and that generates two-dimensional X-ray magnetic circular dichroism (XMCD) data based on the detected transmittance of the transmission X-ray;

piezoelectric devices that control X-, Y- and Z-stages of the analytical section with an accuracy in nanometers which includes the sample-stage of the analytical section; wherein, the apparatus accurately generates two-dimensional XMCD data of each single crystalline-grain contained in the polycrystalline sample by directly measuring transmittance of transmission X-ray passing through the polycrystalline sample even within an external magnet field.

* * * * *